United States Patent [19]

Roggero et al.

[11] Patent Number: 4,980,477
[45] Date of Patent: Dec. 25, 1990

[54] STERICALLY HINDERED 4-OXY-METHYLENE[2-(NORBORN-5-ENYL)]-2,2,6,6-TETRAMETHYL N-SUBSTITUTED-PIPERIDINE DERIVATIVES

[75] Inventors: Arnaldo Roggero, San Donato Milanese; Guglielmo Bertolini, Pavia, both of Italy

[73] Assignees: Eniricerche SpA, Milan; Enichem Synthesis SpA, Palermo, both of Italy

[21] Appl. No.: 517,527

[22] Filed: Apr. 27, 1990

Related U.S. Application Data

[63] Continuation of Ser. No. 240,934, Sep. 6, 1988, abandoned.

[30] Foreign Application Priority Data

Sep. 11, 1987 [IT] Italy ............... 21890 A/87

[51] Int. Cl.$^5$ ............... C07D 211/06; C07D 211/08; C07D 211/44
[52] U.S. Cl. ............... 546/205
[58] Field of Search ............... 546/205

[56] References Cited

U.S. PATENT DOCUMENTS 4,141,883 2/1979 Soma et al. ............... 546/205 X
4,203,890 5/1980 Ramey et al. ............... 546/205 X

OTHER PUBLICATIONS

*Kirk–Othmer Encyclopedia of Chemical Technology*, 2nd Ed., vol. 6, John Wiley, New York, 1965, pp. 692–693.
March, J., *Advanced Organic Chemistry*, McGraw Hill, New York, 1968, pp. 626–627.

*Primary Examiner*—Alan L. Rotman
*Assistant Examiner*—Joseph K. McKane
*Attorney, Agent, or Firm*—Hedman, Gibson, Costigan & Hoare

[57] ABSTRACT

Sterically hindered amino compounds definable by the general formula (I):

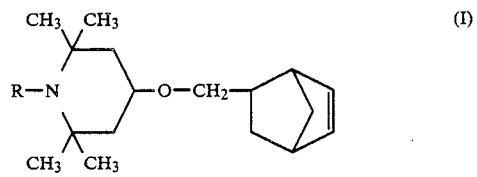

where R represents a hydrogen atom, a $C_1$–$C_{18}$ alkyl radical or a $C_7$–$C_{18}$ alkaryl radical, are useful as organic polymer stabilizers. Processes for preparing these compounds are described.

2 Claims, 1 Drawing Sheet

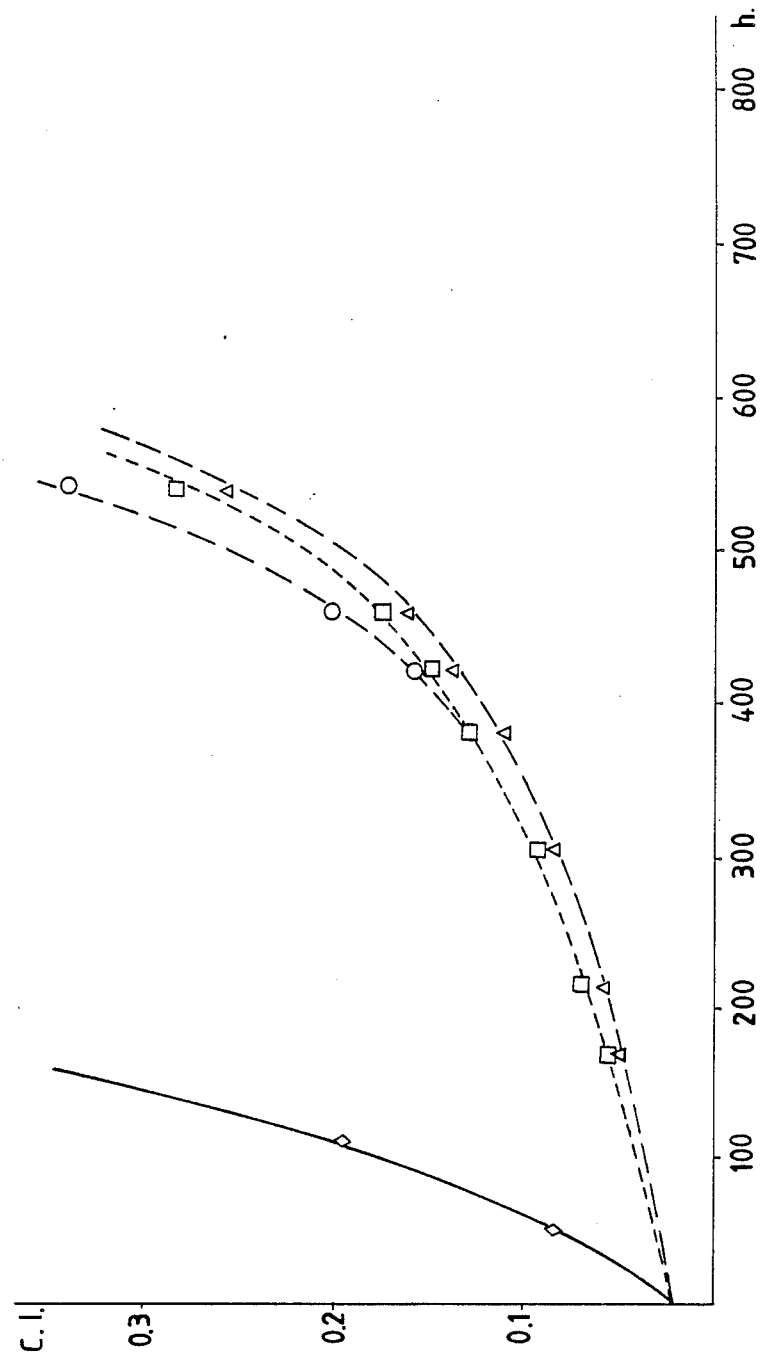

STERICALLY HINDERED 4-OXY-METHYLENE[2-(NORBORN-5-ENYL)]-2,2,6,6-TETRAMETHYL N-SUBSTITUTED-PIPERIDINE DERIVATIVES

CROSS-REFERENCE

This application is a continuation of Ser. No. 07/240,934 filed Sept. 06, 1988, now abandoned.

This invention relates to sterically hindered amino compounds, processes for their preparation and their use in the stabilization of organic polymers.

It is well known that organic polymers undergo degradation with time due to exposure to atmospheric agents and in particular to ultraviolet radiation. To counteract this degradation it is usual in the art to introduce into organic polymers small quantities of stabilizer compounds generally consisting of sterically hindered amines, as described in U.S. Pat. Nos. 3,640,928, 3,840,494 and 4,046,731.

In stabilizing organic compounds with sterically hindered amino compounds there are problems of compatibility between the stabilizer and polymer, and problems due to extractability of the stabilizer from the polymer, this latter phenomenon depending on the molecular weight of the stabilizer used. Certain stabilizer compounds have therefore been proposed having a relatively simple structure but able to convert spontaneously into compounds of complex resinous type in the organic polymer in which they are incorporated, and others of polmer type have been proposed having a similar structure to the polymer to be stabilized as described for example in European patent application Publication No. 162,523 and U.S. patent applications Nos. 910,885 and 057,092.

There is a need for light-stabilizing compounds for polymer materials which besides being thermally stable and compatible with the organic polymer possess at the same time the characteristics of low extractability from the polymer and good mobility within the polymer structure. In this respect, stabilizers possessing such characteristics are particularly suitable for protecting articles of polymer construction having a large surface area, and general polymer-constructed articles requiring a high local stabilizer concentration because of particularly exposed local regions, compared with other less exposed regions.

There is also a need for stabilizer compounds which besides having the aforesaid characteristics can be prepared simply and economically from raw materials which are either commercially available or easily synthesized.

It has now been found that such requirements can be satisfied by the sterically hindered amino compounds of the present invention, which are definable by the general formula (I):

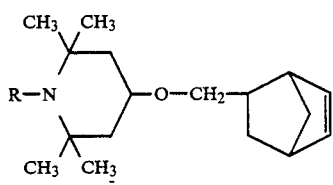

(I)

where R represents a hydrogen atom, a $C_1$–$C_{18}$ alkyl radical or a $C_7$–$C_{18}$ alkayl radical, the alkyl radical being linear or branched.

In the preferred embodiment, in general formula (I) R represents a hydrogen atom or the methyl or benzyl radical.

Consequently, sterically hindered amino compounds preferred for the purposes of the present invention are:
4-oxymethylene-[2'-(norborn-5'-enyl)]-(2,2,6,6-tetramethylpiperidine);
4-oxymethylene-[2'-(norborn-5'-enyl)]-(2,2,6,6-tetramethyl-N-methyl-piperidine); and
4-oxymethylene-[2'-(norborn-5'-enyl)]-(2,2,6,6-tetramethyl-N-benzyl-piperidine).

The sterically hindered amino compounds (I) can be obtained by the Diels-Adler reaction, by reacting cyclopentadiene (II) with a 4-oxy-allyl-2,2,6,6-tetramethyl-piperidine (III):

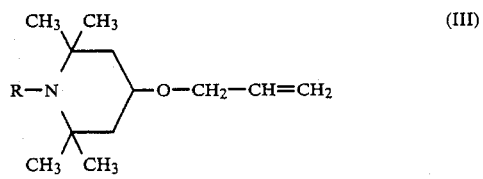

(III)

where R has the aforesaid meaning.

The reaction is conveniently conducted in the liquid phase in an inert organic solvent at a temperature of between 100° C. and 200° C. and preferably of the order of 170° C. at greater than atmospheric pressure, using an excess of compound (II) over its stoichiometric requirement with respect to compound (III), and generally with a ratio of compound (II) to compound (III) of between 1.1:1 and 2.0:1.

Inert organic solvents suitable for this purpose are preferably aliphatic and cycloaliphatic hydrocarbon solvents such as hexane, heptane and cyclohexane.

Under these conditions the time required for the reaction to go to completion is of the order of 1-3 hours.

On termination of the reaction the sterically hindered amino compounds can be recovered from the reaction mixture by normal methods.

In the case of sterically hindered amino compounds (I) in which R is other than hydrogen, the procedure can be carried out by firstly reacting cyclopentadiene with 4-oxy-allyl-2,2,6,6-tetramethyl-piperidine to give 4-oxymethylene-[2'-(norborn-5'-enyl)]-(2,2,6,6-tetramethyl-piperidine) and reacting this latter with an alkyl or alkyl-aryl halide (such as methyl iodide or benzyl chloride) to give the final desired product. This latter reaction is normally conducted in the presence of a hydrohalogen acid acceptor.

The sterically hindered compounds of the present invention are easily mixed and homogenized with organic polymers and have compatibility, mobility and non-extractability especially with regard to styrene polymers and polyolefins.

Thus, according to a further aspect, the present invention relates to compositions stable towards the degradative action of ultraviolet light, which comprise an organic polymer, especially a styrene polymer or a polyolefin, such as polyethylene or polypropylene, and a quantity of sterically hindered amino compound (I) such that the composition contains an active nitrogen quantity of between 0.005% and 0.02% by weight, and preferably of the order of 0.015% by weight.

The term "active nitrogen" signifies the nitrogen contributed by the sterically hindered amino group.

The stabilized polymer compositions of the present invention can be prepared by any known method used for mixing and homogenizing a polymer with a stabilizer.

The experimental examples given hereinafter further illustrate the present invention but without limiting its scope.

EXAMPLE 1

Preparation of 4-oxymethylene-[2'-(norborn-5'-enyl)]-(2,2,6,6-tetramethyl-piperidine):

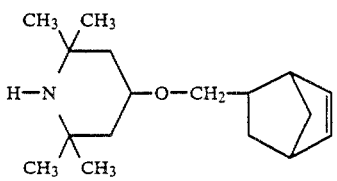

A mixture of 29.0 g (0.15 moles) of 4-oxy-allyl-2,2,6,6-tetramethyl-piperidine and 18, 5 ml (0.225 moles) of cyclopentadiene dissolved in 35 ml of anhydrous n-heptane is drawn under vacuum into a 200 ml autoclave provided with a magnetic stirrer.

The autoclave is immersed in an oil bath heated to 170° C. The reaction is conducted under stirring for three hours.

The crude reaction product is subjected to fractional distillation. Cyclopentadiene, n-heptane and dicyclopentadiene are firstly removed under slight vacuum; 4-oxy-allyl-2,2,6,6-tetramethyl-piperidine is then removed in an unaltered state (boiling point 45° C./0.5 torr) and finally the compound of the title (boiling point 94° C./0.1 torr) is collected in a quantity of 13 g (molar yield 33% with respect to 4-oxy-allyl-2,2,6,6-tetramethyl-piperidine) with a purity of 94% (determined by gas chromatography).

The compound of the title is characterised by mass spectrometry and IR and NMR spectrography. The data deriving from the IR and NMR characterisation are given in Tables I and II respectively.

EXAMPLE 2

Preparation of 4-oxymethylene-[2'-(norborn-5'-enyl)]-(2,2,6,6-tetramethyl-N-methyl-piperidine):

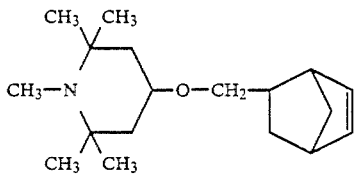

Method A

A mixture of 21.5 g (0.102 moles) of 4-oxy-allyl-2,2,6,6-tetramethyl-N-methyl-piperidine and 12.6 ml (0.153 moles) of cyclopentadiene dissolved in 35 ml of anhydrous n-heptane is drawn under vacuum into a 200 ml autoclave provided with a magnetic stirrer. The autoclave is immersed in an oil bath heated to 170° C. The reaction is conducted under stirring for three hours.

The crude reaction product is subjected to fractional distillation. Cyclopentadiene, n-heptane and dicyclopentadiene are firstly removed under slight vacuum; 4-oxy-allyl-2,2,6,6-tetramethyl-piperidine is then removed in an unaltered state (boiling point 88° C./0.1 torr) and finally the compound of the title (boiling point 143° C./0.1 torr) is collected in a quantity of 9.7 g (molar yield 34% with respect to 4-oxy-allyl-2,2,6,6-tetramethyl-N-methyl-piperidine) with a purity of 95% (determined by gas chromatography).

The compound of the title is characterised by mass spectrometry and IR and NMR spectrography. The data deriving from the IR and NMR characterisation are given in Tables I and II respectively.

Method B 10 g (0.038 moles) of 4-oxymethylene-[2'-(norborn-5'-enyl)]-(2,2,6,6-tetramethyl-piperidine) (prepared as described in Example 1) dissolved in 100 ml of methanol are fed into a 250 ml flask provided with a mechanical stirrer and reflux condenser. 37.5 g (0.264 moles) of methyl iodide and 11.5 g (0.287 moles) of sodium hydroxide are added. The reaction is conducted under reflux conditions for 8 hours and at the end of this time gas chromatography analysis shows that the reaction is complete.

The crude reaction product is treated with water and extracted with ethyl ether. The solvent and volatile substances are removed from the organic phase by evaporation under vacuum to recover 9.1 g (yield 86.4%) of the compound of the title, with characteristics entirely similar to those of the compound prepared by method (A).

EXAMPLE 3

Preparation of 4-oxymethylene-[2'-(norborn-5'-enyl)]-(2,2,6,6-tetramethyl-N-benzyl-piperidine):

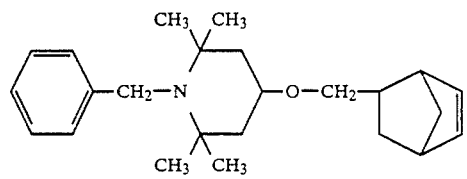

Method A

A mixture of 23 g (0.080 moles) of 4-oxy-allyl-2,2,6,6-tetramethyl-N-benzyl-piperidine and 9,9 ml (0.12 moles) of cyclopentadiene dissolved in 35 ml of anhydrous n-heptane is drawn under vacuum into a 200 ml autoclave provided with a magnetic stirrer. The autoclave is immersed in an oil bath heated to 170° C. The reaction is conducted under stirring for three hours.

The crude reaction product is subjected to fractional distillation. After removing the solvent and unreacted compounds, the compound of the title is recovered as distillation residue in the form of a viscous oil with a molar yield of 37% with respect to 4-oxy-allyl-2,2,6,6-tetramethyl-N-benzyl-piperidine with a purity of 97.6% (determined by gas chromatography).

The compound of the title is characterised by mass spectrometry and IR and NMR spectrography. The data deriving from the IR and NMR characterisation are given in Tables I and II respectively.

Method B 5.0 g (0.019 moles) of 4-oxymethylene-[2'-(norborn-5'-enyl)]-(2,2,6,6-tetramethyl-piperidine) (prepared as described in Example 1) and 6.5 g (0.051 moles) of benzyl chloride are fed into a flask provided with a mechanical stirrer and reflux condenser. The reaction is conducted for 5 hours at 150° C. and at the end of this time gas chromatography analysis shows that the reaction is complete.

The crude reaction product is treated in the same manner as in method (A) to recover 6.04 g (yield 90%) of the compound of the title, with characteristics entirely similar to those of the compound prepared by method (A).

spectroscopy. The results of the test are given in the graph of the Figure, in which the horizontal axis represents the residence time in UV CON in hours and the vertical axis represents the carbonyl index.

In this graph:
- ◇—◇ is the curve for polyethylene film as such;
- ○—○ is the curve for polyethylene film containing the compound of Example 2;
- □—□ is the curve for polyethylene film containing the compound of Example 3; and
- △—△ is the curve for polyethylene film containing the compound of Example 1.

We claim:

1. A compound of the formula:

TABLE I

| Compound Ex. No. | $\nu$ N—H | $\nu$ =C—H | $\nu$ C=C | $\nu$ C=C | $\delta$ symm $CH_3$ | $CH_3$ r | $\beta$ =C—H | $\nu$ C—O | $\gamma$ =C—H |
|---|---|---|---|---|---|---|---|---|---|
| (1) | 3135 | 3130 | 1643 | — | 1374 | 1274 | — | 1094 | 718 |
|  |  | 3055 |  |  | 1363 | 1190 |  |  |  |
| (2) | — | 3130 | — | — | 1372 | 1252 | — | 1094 | 717 |
|  |  | 3050 |  |  | 1358 | 1180 |  |  |  |
| (3) | — | 3195 | — | 1602 | 1381 | 1258 | 1171 | 1096 | 740 |
|  |  | 3100 |  | 1584 | 1368 | 1180 | 1025 |  | 719 |
|  |  | 3084 |  | 1493 |  |  |  |  | 696 |
|  |  | 3060 |  |  |  |  |  |  |  |
|  |  | 3025 |  |  |  |  |  |  |  |

TABLE II

Chemical shifts (ppm by TMS)

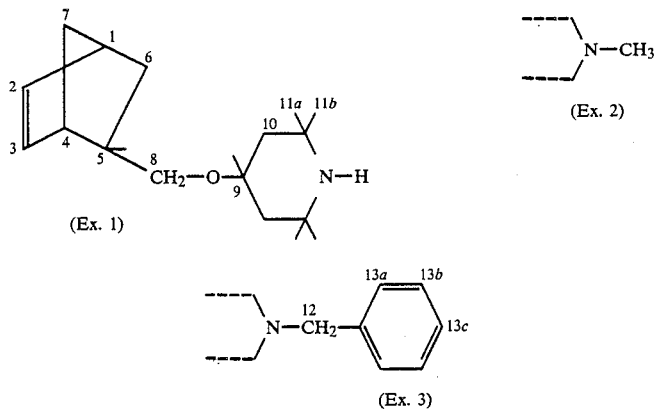

| Ex. No. | Compound 1 | 2 | 3 | 4 | 5 | 6 | 7 | 8 | 9 | 10 | 11a | 11b | 12 | 13a | 13b | 13c |
|---|---|---|---|---|---|---|---|---|---|---|---|---|---|---|---|---|
| (1) | 2.8 | 5.96 | 6.15 | 2.93 | 2.32 | 1.86 | 1.3 | 3.17 | 3.6 | 1.8 | 1.1 | 1.14 | — | — | — | — |
| (2) | 2.76 | 5.95 | 6.12 | 2.9 | 2.35 | 1.85 | 1.3 | 3.1 | 3.45 | 1.83 | 1.0 | 1.15 | — | — | — | — |
| (3) | 2.8 | 5.96 | 6.15 | 2.93 | 2.35 | 1.88 | 1.3 | 3.19 | 3.6 | 1.8 | 1.1 | 1.14 | 3.8 | 7.42 | 7.25 | 7.1 |

The compounds prepared in Examples 1, 2 and 3 are added to the commercial polyethylene RIBLENE® A42CL of Messrs. ENICHEM in a quantity such as to provide an active N content of 0.015% by weight in the polymer.

Homogenization is obtained by two extrusion passes through an MFI apparatus.

The compositions are pressed to form films of 110 μ thickness. The films thus obtained are subjected to an accelerated ageing test in UV CON with irradiation cycles of 8 hours at 60° C. with a fluorescent lamp (UV radiation between 280 and 350 nm) and 4 hours of condensation in the dark at 40° C.

The degradation is evaluated on the basis of the increase in the carbonyl index, which is measured by IR

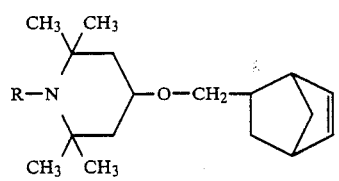

(I)

wherein R represents a hydrogen atom, a $C_1$–$C_{18}$ linear or branched alkyl radical, or a $C_7$–$C_{18}$ aralkyl radical.

2. The compound according to claim 1 wherein R represents the hydrogen atom, the methyl radical, or the benzyl radical.

* * * * *